US006271404B1

(12) United States Patent
Bhaggan et al.

(10) Patent No.: US 6,271,404 B1
(45) Date of Patent: Aug. 7, 2001

(54) PRODUCTION OF MATERIALS RICH IN CONJUGATED ISOMERS OF LONG CHAIN POLYUNSATURATED FATTY ACID RESIDUES

(75) Inventors: Krish Bhaggan; Frederick William Cain; John Bernard Harris; Victoria Taran, all of Wormerveer (NL)

(73) Assignee: Unilever Patent Holdings B.V., Vlaardingen (NL)

( * ) Notice: Subject to any disclaimer, the term of this patent is extended or adjusted under 35 U.S.C. 154(b) by 0 days.

(21) Appl. No.: 09/617,510

(22) Filed: Jul. 14, 2000

Related U.S. Application Data

(63) Continuation of application No. 09/151,776, filed on Sep. 11, 1998, now Pat. No. 6,160,140.

(30) Foreign Application Priority Data

Sep. 12, 1997 (EP) .................................................. 97307110

(51) Int. Cl.⁷ .................................................. C07B 35/08
(52) U.S. Cl. .............................................................. 554/126
(58) Field of Search ................................................ 554/126

(56) References Cited

U.S. PATENT DOCUMENTS

| 2,242,230 | 5/1941 | Burr . | |
| 2,343,644 | 3/1944 | Cawley | 260/405.6 |
| 5,208,356 | 5/1993 | Pariza et al. | 554/79 |
| 5,760,082 | 6/1998 | Cook et al. | 514/560 |
| 5,814,663 | 9/1998 | Cook et al. | 514/560 |
| 5,986,116 | 11/1999 | Iwata et al. | 554/126 |
| 6,015,833 | 1/2000 | Saebo et al. | 514/558 |
| 6,060,514 | 5/2000 | Jerome et al. | 514/560 |

FOREIGN PATENT DOCUMENTS

| 0 779 033 A1 | 6/1997 | (EP) . |
| 0 839 897 A1 | 5/1998 | (EP) . |
| WO 97/46118 | 12/1997 | (WO) . |
| WO 97/46230 | 12/1997 | (WO) . |

Primary Examiner—Deborah D. Carr
(74) Attorney, Agent, or Firm—Pillsbury Winthrop LLP

(57) ABSTRACT

The invention concerns an isomerisation process, wherein materials comprising non-congugated long chain polyunsaturated fatty acids are subjected to base in the presence of an alcohol with ≧3 C-atoms and ≧2 OH groups and having ratio C-atoms: OH-groups of ≧1.25. The resulting reaction product, containing the conjugated isomers is obtained in higher yield at lower temperatures and are not contaminated by presence of non food grade solvent.

8 Claims, No Drawings

PRODUCTION OF MATERIALS RICH IN CONJUGATED ISOMERS OF LONG CHAIN POLYUNSATURATED FATTY ACID RESIDUES

This is a continuation of application Ser. No. 09/151,776, filed Sep. 11, 1998 now U.S. Pat. No. 6,160,140.

Materials comprising mainly (mainly meaning more than 40% preferably more than 60%) conjugated isomers of long chain polyunsaturated fatty acids are known for their health performance, when applied in food products. In general these products comprise the linoleic acid isomers and from all the different linoleic acid isomers possible the cis 9 trans 11 and trans 10 cis 12 isomers are most often the most abundantly present in these materials, in general in a 1:1 weight ratio.

These products with high contents of different conjugated isomers of the same long chain polyunsaturated fatty acid are useful starting materials for the preparation of materials with other ratio's of the different conjugated isomers of the long chain polyunsaturated fatty acids. Such a process could enable us to prepare products with a limited number of isomers and with very high ratio's of the different isomers of the conjugated polyunsaturated acids. Therefore such a process could enable us to take advantage of the different properties of the different isomers for different purposes.

A process to enrich the mix containing the different conjugated isomers of the same long chain polyunsaturated fatty acid in one of the isomers is the subject of our earlier WO patent application WO 97/18320.

The prior art processes for the preparation of above starting materials rich in conjugated polyunsaturated long chain fatty acids have however a number of drawbacks.

According to a first prior art method this material can be made by a process wherein water has to be used as solvent at high pressures and rather high temperatures, resulting in a product wherein far too many isomers of the polyunsaturated fatty acid are present.

This means that the product per se, but also the product as a starting material for the enrichment contains too many components. Therefore the product per se is less useful as food ingredient, while also the products obtained after the enrichment process are rather contaminated.

Alternatively the prior art (EP799033) discloses a process, wherein an organic solvent in this case ethylene glycol has to be used. Ethylene glycol however has one main drawback, ie it is not foodgrade and it is very difficult to remove it completely from the reaction product of the isomerisation process.

This means that the product per se, but also later products made from it like the enrichment products, are not food grade either.

Moreover the yields of desired conjugated polyunsaturated isomers in the reaction product of the conversion in the presence of base are rather low in that instance.

According to an example 1 of a non-prepublished PCT-application with an earlier priority date (WO97/46230) conjugated linoleic acids can be obtained by isomeration of linoleic acid or safflower oil by subjecting the starting material to base (KOH) in propylene glycol at 180° C. for 20 minutes. When we performed this process, we found that the reaction product contained relatively large amounts of other isomers, than the desired conjugated linoleic isomers as well. This probably is due to the severe reaction, conditions applied.

According to another non-published patent application with an earlier priority date (EP 839897) conjugated linoleic acids can be obtained by subjecting fats, containing linoleic acid to base in propylene glycol. Hower high ratios of base to solvent (6 mole/l) are applied. Moreover the use of fats as starting material has the disadvantage over using free fatty acid as staring material, that a build-up of glycerol in the solvent occurs, when the solvent is recycled in the reaction-system.

We found a solution for the above problems that even had another big unexpected advantage. We found that with our new process not only the yields were higher at lower temperatures, while the use of a non-foodgrade solvent could be avoided, but we also found surprisingly that the number of isomers formed was less and that the isomers formed by a subsequent enzymic enrichment process could be separated easier than when ethylene glycol was used as a solvent.

Therefore our invention concerns in the first instance a process for the preparation of materials comprising mainly conjugated isomers of long chain polyunsaturated fatty acids wherein an oil or a free fatty acid composition or an alkyl ester composition thereof, containing at least 25 wt % of at least one isomer other than the conjugated isomers of long chain polyunsaturated fatty acids is subjected to a treatment with a base in a solvent and wherein the solvent is an alcohol with at least 3 C-atoms and at least two hydroxy groups having:

a ratio of number of C-atoms: number of OH groups of at least 1.25 but less than 3.5, preferably from 1.5 to 2.75, while the reaction is carried out between 100 and 180° C., more preferably between 120 and 180° C. This temperature range thus does not include 180° C. per se.

A very suitable solvent is 1.3 dihydroxypropane or 1,2 dihydroxypropane. These solvents are foodgrade so that traces left in the products are not harmful.

The reaction is preferably performed in the absence of glycerol. Herefore free fatty acids are preferably used as starting material.

The base could be any base but we found that the best results were obtained with NaOH or KOH as base. Suitable concentrations for the base are greater than 0.25 mole/l of solvent, preferably 0.25–3.5 most preferably 1.25–2.75 mole/l. Using higher amounts of base leads to the formation of products, wherein many isomers (in particular $C_{18:2}$ trans/trans-isomers) are present (cf our comparative example)

The starting materials for our novel process have to contain at least 25 wt % of at least one isomer other than the conjugated isomers of long chain polyunsaturated fatty acids. This amount preferably is more than 40 wt %, more preferably even more than 60 wt %. The long chain polyunsaturated fatty acids preferably have at least two unsaturations and at least 18 C-atoms. The most preferred polyunsaturated long chain fatty acids are the different linoleic and linolenic acid isomers. Linoleic acid eg contains mainly the cis 9 cis 12 diunsaturated carbon chain, while in the different natural occurring linolenic acids the three double bonds are all cis but occur at different positions (non-conjugated) in the carbon chain.

Very suitable starting materials are selected from the group consisting of: sunflower oil, rape seed oil, soybean oil, safflower oil, linseed oil(=high in $C_{18:3}$) and in particular the free acids derived from these oils and alkylesters from these free acids. These materials are rich in linoleic acid or linolenic acid, in particular $C_{18:2}$, cis 9 cis 12.

The most preferred products of our novel process are products that contain the linoleic isomers cis 9 trans 11 and trans 10 cis 12 in about a 1:1 ratio. As disclosed in our earlier WO application 97/18320 these materials can be converted into materials wherein this ratio cis 9 trans 11: trans 10 cis 12 is changed considerably. Our products are suitably isolated from the crude reaction mixture by the addition of diluted acid to the soap formed until an acidic pH is achieved (preferably: pH 1–3), whereupon the oil is separated from the waterlayer and dried.

According to a last embodiment of our invention we claim the use of an oil, or of free fatty acids derived from this oil, or of alkyl esters from these free fatty acids comprising mainly conjugated isomers of long chain polyunsaturated fatty acids for the preparation of a material comprising mainly conjugated isomers of the long chain polyunsaturated fatty acids in another ratio for the conjugated isomers by an enzymic enrichment process using an enzyme that has the ability to discriminate between different isomers of conjugated long chain polyunsaturated fatty acids, wherein the product obtained from the process according to claims 1–5 is applied as starting material in the enzymic enrichment process for the production of the materials with the other ratio of conjugated isomers.

EXAMPLE I (=Comparative)

31 grams of safflower oil were added to a solution of 9.0 grams of NaOH pellets (dissolved by stirring at 60° C.) in 150 gram of ethylene glycol.

The mixture was heated to 135° C., while it was stirred in an inert atmosphere.

Samples of 2 ml were collected after 2,19,25 and 49 hours.

After 49 hours the reaction mix was cooled to 60° C. and the soap was split with 80 ml of diluted sulphuric acid (diluted 1:10 with distilled water). The pH of the final mix was 1.5.

The oil was separated from the water phase and dried over Na2SO4.

The oil product was analysed with high resolution FAME GC. All materials were analysed in the same way.

The intermediate samples removed during the process were worked in the same way and the oil obtained was also analysed by high resolution FAME GC.

The results are given below.

TABLE I

COMPOSITION OF STARTING OIL

| component | name | wt % |
|---|---|---|
| C18:2 | linoleic acid c9, c12 | 74.8 |
| C18:1 | oleic acid | 14.1 |
| C18:0 | stearic acid | 2.7 |
| C16:0 | palmitic acid | 6.7 |
| others | | 1.7 |

TABLE II

PRODUCT AFTER 49 HRS

| component | wt % |
|---|---|
| C18:2 c9, t11 | 28.6 |
| C18:2 t10, c12 | 28.7 |
| C18:2 others conj | 1.6 |

TABLE II-continued

PRODUCT AFTER 49 HRS

| component | wt % |
|---|---|
| unidentified | 0.3 |
| C18:2 c9, c12 | 16.4 |
| C18:1 | 14.2 |
| C18:0 | 2.7 |
| C16:0 | 6.9 |
| others | 0.6 |

TABLE III

Composition of the samples removed intermediately

| time in hrs | c9, t11 | t10, c12 | C18:2 | conversion |
|---|---|---|---|---|
| 2 | 3.0 | 2.9 | 70.4 | 5.7 |
| 19 | 18.1 | 18.3 | 38.4 | 48.7 |
| 25 | 21.7 | 22.0 | 30.9 | 58.7 |
| 49 | 28.2 | 28.5 | 16.3 | 78.2 |

EXAMPLE II

Example I was repeated however 1,2 dihydroxy propane was used as solvent.

The results are summarized in the tables IV and V

TABLE IV

PRODUCT AFTER 49 HRS

| component | wt % |
|---|---|
| C18:2 c9, t11 | 35.6 |
| C18:2 t10, c12 | 34.9 |
| C18:2 others conj. | 2.1 |
| unidentified | 0.4 |
| C18:2, c9, c12 | 2.5 |
| C18:1 | 14.2 |
| C18:0 | 2.7 |
| C16:0 | 6.9 |
| others | 0.6 |

TABLE V composition of the samples removed intermediately.

| time in hrs | c9, t11 | t10, c12 | C18:2 | conversion |
|---|---|---|---|---|
| 2 | 6.5 | 6.3 | 63.2 | 15.5 |
| 19 | 29.8 | 29.4 | 15.0 | 79.9 |
| 25 | 32.8 | 32.2 | 8.9 | 88.1 |
| 49 | 35.3 | 34.4 | 2.5 | 96.7 |

EXAMPLE III (Comparative)

Equipment 60 liter autoclave with electrical heating for 250 deg. C. and capable of pressures more than 50 bar. The autoclave has a gate stirrer. It is made from 316 stainless steel.

Method 30 kgs of a 4 molar aq. solution of sodium hydroxide solution was made up in the autoclave. The solution was heated to 60 deg. C. and then 30 kgs of Safflower oil were slowly added whilst stirring.

The stirred autoclave was then heated up to 230 deg. C. This took 5 hours and then maintained at 230 deg.C for a further 1.5 hours at which point the autoclave was cooled in 1 hour to 90 deg. C. The reacted mixture was then run out of the autoclave into a drum and mixed with an equal quantity of hot water.

To obtain the free fatty acid product, the soap produced in the reactor was split with acid. With the soap solution at between 90 and 100 deg. C., 1N sulphuric acid was slowly added and stirred until the pH was less than 3, at which point the soap reacted to produce free fatty acid which could then allowed to separate and then decanted off.

Results

The Safflower originally contained 76.6% of linoleic acid (cis-9,cis-12). Of this more than 90% was conjugated to give the following interpretation on High Res GLC:

|  | Feed oil | Conjugated |
| --- | --- | --- |
| 14:0 | 0.1 | 0.1 |
| 16:0 | 6.8 | 6.9 |
| 18:0 | 2.5 | 2.6 |
| 18:1 | 13.4 | 13.3 |
| 18:2 c9/c12 | 76.6 | 4.7 |
| 20+ | 0.6 | 0.8 |
| CLA c9t11 | — | 27.9 |
| CLA t10c12 | — | 20.3 |
| CLA others | — | 23.4 |

EXAMPLE IV (Comparative)

30 grams of safflower oil were added to a solution of 75.1 grams of KOH pellets (dissolved by stirring at 100° C.) in 150.1 grams of propylene glycol. (ratio of base: solvent: 9 mole/l).

The mixture was heated to 135° C., while it was stirred in an inert atmosphere. After 16.5 hours the reaction mix became very thick and the reaction was stopped. The sample from the end mixture was taken and the soap was splitted with diluted sulphuric acid (diluted 1:10 with distilled water) until the pH of the water phase was 1.5. The oil was separated from the water phase and dried over $Na_2SO_4$. The oil was analyzed by high resolution FAME GC.

TABLE

PRODUCT AFTER 16.5 HRS

| component | wt % |
| --- | --- |
| C14:0 | 0.13 |
| C16:0 | 7.55 |
| C16:1 | 0.13 |
| C17:0 | 0.05 |
| C18:0 | 2.86 |
| C18:1 | 11.81 |
| C18:2 | 1.21 |
| C20:0 | 0.04 |
| C18:3 | 0.33 |
| C20:1 | 0.21 |
| C18:2 c9, t11 | 22.32 |
| C18:2 c11, t13 | 2.65 |
| C18:2 t10, c12 | 21.31 |
| C18:2 c, c | 4.07 |
| C18:2 t, t | 23.48 |
| C18:2 oxid | 0.20 |
| C22:0 | 0.22 |
| others | 1.43 |

EXAMPLE V 30 g of KOH were dissolved in 200 ml of 1,2 dihydroxypropane (=2.7 mole/l). 30 g of free fatty acids from safflower oil were added to this mixture and were reacted under nitrogen at 135° C. for 47 hrs. The soap formed was worked up with diluted sulfuric acid (10%). The product obtained was analysed by GLC and the following product composition was found:

| component | wt % |
| --- | --- |
| C14:0 | 0.2 |
| C16:0 | 4.2 |
| C18:0 | 1.6 |
| C18:1 | 22.5 |
| C18:2t | 1.6 |
| C18:2c | 24.0 |
| C18:2c9t11 | 20.7 |
| C18:2c11t13 | 0.6 |
| C18:2t10c12 | 20.3 |
| C18:2 9, 11 cc | 0.6 |
| C18:2 10, 12 cc | 0.6 |

EXAMPLE VI 210 g of NaOH was dissolved in 2100 ml 1,2 dihydroxypropane.(=2.5 mole/l). 700 g of free fatty acids from sunflower oil were added to this mixture and were reacted for 47 hrs at 135° C. The soap formed was worked up by adding a diluted (10%) sulfiric acid solution until pH=2. The product obtained was analysed by GLC. The composition of the product was:

| component | % in product | in starting FFA |
| --- | --- | --- |
| C14:0 | 0.2 | 0.2 |
| C16:0 | 3.8 | 3.9 |
| C18:0 | 1.5 | 1.5 |
| C18:1 | 22.0 | 21.9 |
| C18:2 c9c12 | 7.6 | 71.5 |
| C18:2 c9t11 | 30.6 | — |
| C18:2 c11t13 | 0.5 | — |
| C18:2 t10c12 | 30.3 | — |
| C18:2 c9c11 | 0.7 | — |
| C18:2 c10c12 | 0.7 | — |

What is claimed is:

1. Process for the preparation of materials comprising mainly conjugated isomers of long chain polyunsaturated fatty acids which comprises treating a starting material comprising a free fatty acid composition or an alkyl ester composition thereof, containing at least 25 wt % of at least one isomer other than the conjugated isomers of long chain polyunsaturated fatty acids with a base in a solvent at a temperature between 100° C. and 180° C. wherein the solvent is an alcohol with at least 3 C-atoms and at least two hydroxy groups having a ratio of number of C-atoms: number of OH groups of at least 1.25 but less than 3.5, the base being utilized in a concentration of 0.25 mole/l–3.5 mole/l) solvent.

2. Process according to claim 1, wherein the solvent is 1,3 dihydroxy propane or 1,2 dihydroxy propane.

3. Process according to claim 2, wherein the base is NaOH or KOH.

4. Process according to claim 1, wherein the starting material contains at least 40 wt % of long chain-polyunsaturated fatty acid, containing at least two unsaturations and at least 18 C-atoms.

5. Process according to claim 4, wherein the starting material is selected from the group consisting of the free fatty acids of sunflower oil, rape seed oil, soybean oil, safflower oil, linseed oil and alkylesters of these free acids.

6. Process according to claim 1 wherein the ratio of C-atoms to OH groups is from 1.5 to 2.75.

7. Process according to claim 1 wherein the starting material contains at least 60 wt % of long chain polyunsaturated fatty acid.

8. Process for the preparation of materials comprising mainly conjugated isomers of long chain polyunsaturated fatty acids which comprises treating a starting material comprising a free fatty acid composition or an alkyl ester composition thereof, containing at least 25 wt % of at least one isomer other than the conjugated isomers of long chain polyunsaturated fatty acids with a base in a solvent wherein the solvent is an alcohol with at least 3 C-atoms and at least two hydroxy groups having a ratio of number of C-atoms: number of OH groups of at least 1.25 but less than 3.5.

\* \* \* \* \*